United States Patent [19]

Müller et al.

[11] Patent Number: 5,082,865
[45] Date of Patent: * Jan. 21, 1992

[54] AVAROL AND ITS PRODUCTION AND USE AS AN ANTITUMOR AGENT (I)

[76] Inventors: Werner E. G. Müller, Semmelweisstr. 12, 6200 Wiesbaden-Biebrich; Rudolf K. Zahn, Oderstr. 12, 6200 Wiesbaden; Eckart Eich, Rosmerthastr. 84, 6500 Mainz 21, all of Fed. Rep. of Germany

[ * ] Notice: The portion of the term of this patent subsequent to Aug. 7, 2007 has been disclaimed.

[21] Appl. No.: 458,948

[22] Filed: Dec. 29, 1989

Related U.S. Application Data

[62] Division of Ser. No. 820,440, Jan. 17, 1986, Pat. No. 4,946,869.

[51] Int. Cl.$^5$ .......................................... A61K 31/045
[52] U.S. Cl. ..................................................... 514/729
[58] Field of Search ........................................ 514/729

[56] References Cited

PUBLICATIONS

Comp. Biochem. Physiol. 71B, pp. 281–283 (1982).
Tetrahedron Letters 38, pp. 3401–3404 (1974) by Pergamon Press.
Experientia 38, p. 896 (1982).
Chemical Abstracts 97, p. 462, item 97:21000t (1982).
Kurelec, B. et al., "Antimutagenic Activity of the Novel Antileukemic Agents, Avarone and Avarol", Mutation Research, 144 (1985), pp. 63–66.
Müller, W. E. G., "Potent Antileukemic Activity of the Novel Cytostatic Agent Avarone and its Analogues in Vitro and in Vivo", Cancer Research 45 (1985), pp. 1–5.
Müller, W. E. G. et al., "Avarol, A Cytostatically Active Compound from the Marine Sponge *Dysidea avara*", Comp. Biochem. Physiol. 80C, No. 1, (Jan. 31, 1985), pp. 47–52.
Müller, W. E. G. et al., J. Antibiotics 37, 239 (1984).
Cariello, L. et al., "Developmental Aberrations in Sea-Urchin Eggs Induced by Avarol and Two Cogeners, the Main Sesquitterpenoid Hydroquinones from the Marine Sponge, *Dysidea avara*", Comp. Biochem, Physiol., 65C, pp. 37–41 (1980).

Primary Examiner—Jerome D. Goldberg

[57] ABSTRACT

The antitumor compound avarol, a process for its production, pharmaceutical compositions containing said compound, and a method of combating tumors therewith, are disclosed.

3 Claims, 1 Drawing Sheet

AVAROL AND ITS PRODUCTION AND USE AS AN ANTITUMOR AGENT (I)

This is a division of application Ser. No. 820,440, filed Jan. 17, 1986, now U.S. Pat. No. 4,946,869, issued Aug. 7, 1990.

BACKGROUND OF INVENTION

1. Field of Invention

Antitumor compositions comprising avarol and method of employing avarol for its antitumor activity; method of and ameliorating, alleviating, or palliating tumorous and/or cancerous conditions therewith; method of production of the active principles avarol. In brief, pharmaceutical compositions embodying avarol, method of treating with avarol, and employment of the said active principles for its anticarcinogenic activity as.

It is to be understood that, any suggestion in this application to the contrary notwithstanding, the present invention is directed only to a method of combating tumor cells, the growth of which is adversely affected by Avarol and therefore susceptible thereto, comprising the step of administering to the host an effective antitumor amount of Avarol, advantageously in the form of a pharmaceutical composition thereof in which it is present together with a pharmaceutically-acceptable carrier or diluent, and to antitumor pharmaceutical compositions which are effective and therefore useful for such purpose.

2. Prior Art

Avarone and its hydroquinone derivative avarol are natural substances found in the marine sponge Dysidea avara (L. Minale, R. Riccio and G. Sodano, Tetrahedron Letters 1974, 3401–3404; S. de Rosa, L. Minale, R. Riccio and G. Sodano, J. Chem. Soc. Perkin I, 1408–1414 (1976)). These compounds were isolated from a diethyl ether extract using column chromatography on silica gel (L. Cariello, M. de Nicola Giudici and L. Zanetti, Comp. Biochem. Physiol. 65c, 37–41 (1980)). With regard to biological effects it has so far only been known that avarol in very high concentrations (130 $\mu$m) affects the cells of the sea urchin embryo, causing "developmental abberations" (L. Cariello et al., ibid.). The derivatives described in the literature are, among others, the 3'-methylamino and the 4'-methylaminoavarone (G. Cimino, S. de Rosa, S. de Stefano, L. Cariello and L. Zanetti, Experientia 38, 896 (1982) as well as the avarol dimethyl ether and the avarol diacetate (S. de Rosa et al., ibid.).

THE PRESENT INVENTION

It has now been found that avarol has pronounced and unpredictable antitumoral properties. Owing to the aforementioned properties, this substance is suited for the treatment of carcinoses, either as such or in the form of a prodrug or precursor or any of the foregoing in the form of a pharmaceutical composition where present together with a pharmaceutically-acceptable diluent or carrier.

It is to be understood that, any suggestion in this application to the contrary notwithstanding, the present invention is directed only to a method of combating tumor cells, the growth of which is adversely affected by Avarol and therefore susceptible thereto, comprising the step of administering to the host an effective antitumor amount of Avarol, advantageously in the form of a pharmaceutical composition thereof in which it is present together with a pharmaceutically-acceptable carrier or diluent, and to antitumor pharmaceutical compositions which are effective and therefore useful for such purpose.

OBJECTS OF THE INVENTION

It is an object of the present invention to provide novel pharmaceutical compositions embodying avarol or a pro-drug or precursor thereof or therefore. It is a further object of the invention to provide a novel method of treating, eliminating, alleviating, palliating, or ameliorating undesirable tumorous or cancerous, conditions by the employment of avarol or a pharmaceutical composition containing the same. An additional object of the invention is the provision of a process for producing the active principle avarol. Still additional objects will become apparent hereinafter, and still further objects will be apparent to one skilled in the art.

SUMMARY OF THE INVENTION

It is to be understood that, any suggestion in this application to the contrary notwithstanding, the present invention is directed only to a method of combating tumor cells, the growth of which is adversely affected by Avarol and therefore susceptible thereto, comprising the step of administering to the host an effective antitumor amount of Avarol, advantageously in the form of a pharmaceutical composition thereof in which it is present together with a pharmaceutically-acceptable carrier or diluent, and to antitumor pharmaceutical compositions which are effective and therefore useful for such purpose.

What we therefore believe to be comprised by our invention may be summarized inter alia in the following words:

A pharmaceutical composition suitable for use as an antitumor composition comprising an effective antitumor amount of avarol together with a pharmaceutically-acceptable pharmaceutical carrier; also a method of combating a tumor comprising administering to the host or situs an effective antitumor amount of avarol; and such a method wherein the compound is administered in the form of a pharmaceutical composition thereof, in which it is present together with a pharmaceutically-acceptable carrier or diluent. Finally a pharmaceutical composition suitable for use as an antitumor composition comprising an effective antitumor amount of avarol together with a pharmaceutically-acceptable pharmaceutical carrier and a method of combating a tumor comprising administering to the host or situs an effective antitumor amount of avarol.

It is to be understood that, any suggestion in this application to the contrary notwithstanding, the present invention is directed only to a method of combating tumor cells, the growth of which is adversely affected by Avarol and therefore susceptible thereto, comprising the step of administering to the host an effective antitumor amount of Avarol, advantageously in the form of a pharmaceutical composition thereof in which it is present together with a pharmaceutically-acceptable carrier or diluent, and to antitumor pharmaceutical compositions which are effective and therefore useful for such purpose.

IDENTITY

The active antitumor ingredients or agents of the present invention have the formulas:

2-[(1R)-1,2,3,4,4a,7,8,8aα-octahydro-1β,2β,4aβ,5-tetramethyl-1-naphthylmethyl]-quinone

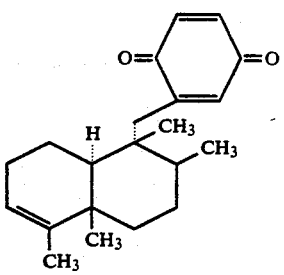

Formula of Avarone
$C_{21}H_{28}O_2$; Mol wt: 312,20
C 80.73%; H 9.03%: O 10.24%

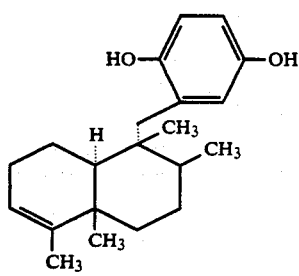

Its derivative Avarol
$C_{21}H_{30}O_2$; Mol wt: 314.22
C 80.32%; H 9.81%; O 9.87%

History

Sponges live in symbiosis with algae, fungi, bryozoae and bacteria (Muller et al, F. Bacteriol. 1981, 145, pp. 548-558). Experimental data support the hypothesis that the symbiotic relationship between sponge and non-sponge cells is based on a growth-promoting (e.g., lectin) and a growth-inhibiting principle (cytostatic agent). One derivative of the cytostatic agent 1-β-D-arabinofuranosylthymine, isolated from the sponge Cryptothethya crypta, has already been established as an anti-cancer agent in the clinic (1-β-D-arabinofuranosylcytosine) (Muller et al., Jap. J. Antibiotics 1977, 30 Supp. pp. S104-S120). In the course of our screening program for antimitotic agents, it was found that the sponge secondary metabolites Avarone and Avarol exhibit antimitotic activity, which is different than that of Vincristine [Oncovin ®], Colchicine, or 4'-Demethylepipodophyllotoxin-9-(4,6-0-ethylidene-β-D-glucopyranoside) [Etoposide ®].

Isolation and Synthesis

Avarol has been isolated from the marine sponge Dysidea avara, which is ubiquitous near the Atlantic coast of Europe, in the Mediterranean and around the Maldive Islands (Minale et al., Tetrahedron Lett. 1974, No. 36, pp. 3401-3404). According to our present process, ground, chopped, or otherwise comminuted material is extracted with ethyl acetate. The organic phase is dried over $MgSO_4$ and then evaporated to dryness yielding a tar-like residue. This material is taken up in benzene and purified by silica gel column chromatography using benzene/10% ethyl acetate as solvent. The Avarol fractions are concentrated; purified Avarol is obtained after several crystallizations from acetone-methylene chloride. Yield: 2.7 g of Avarol from 1 kg of fresh material. Avarone may be obtained from its corresponding hydroquinone Avarol by $Ag_2O$ oxidation, but it is preferably obtained by column separation according to our new process, represented by Example 1 hereinafter.

Description

Avarone: Yellowish-brownish crystals; m.p. 62°-64° C. (hexane); slightly soluble in water; solubility in dimethylsulfoxide >100 mg/ml at 23° C.; stable in solution when stored at 4° C. for up to 1 year.

Avarol: Whitish crystals; m.p. 146°-148° C. (chloroform); other characteristics same as for Avarone.

PRODRUGS OR PRECURSORS AND THEIR PREPARATION

The compounds avarone and avarol may also be employed or embodied in pharmaceutical compositions according to the invention in the form of compounds which convert to avarone or avarol after administration to the living animal body. Such compounds are commonly referred to today as prodrugs or precursors, and representative examples include esters of avarol and alkylamino derivatives of avarone. As already indicated, some of these compounds are known in the prior art, whereas others are made in a known manner corresponding thereto. Representative of such prodrugs and precursors, and their preparation, are set forth in the following.

The active ingredients of the present invention, and their precursors or prodrugs, are accordingly avarone, avarol, and their derivatives of the general formula I

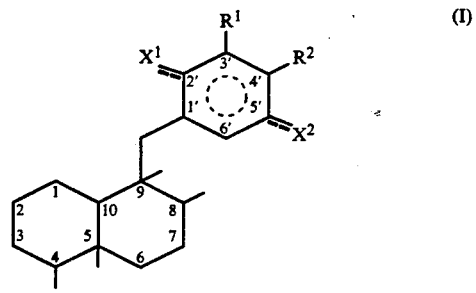

wherein

1. $X^1$ and $X^2$ is oxo with double bonds between C-1' and C-6', and between C-3' and C-4';
   $R^1$ is hydrogen
   and
   $R^2$ is alkyl amino having one, two, three or four C atoms;
   or wherein 2. $X^1$ and $X^2$ is oxo with double bonds between C-1' and C-6', and between C-3' and C-4';
   $R^1$ is alkyl amino having one, two, three or four C atoms,
   and
   $R^2$ is hydrogen;
   or wherein 3. $X^1$ and $X^2$ is hydroxy or acyloxy with 2-6C atoms or $X^1$ with $X^2$ is diacyloxy with 4-6C atoms with aromatic ring;
   and
   $R^1$ and $R^2$ is hydrogen, 4. Avarone- As in 1 or 2, but both $R^1$ and $R^2$ being hydrogen, and 5. Avarol - As in 3, both $X^1$ and $X^2$ being hydroxy, as well as salts of the alkylaminoavarones as conventionally obtained by reaction with physiologically-tolerable acids.

The compounds of formula I thus comprise avarone ($R^1=R^2=H$ in Formula Ia) and alkylaminoavarone derivatives thereof, as well as avarol ($R^1=R^2=H$ in Formula Ib) and esters thereof.

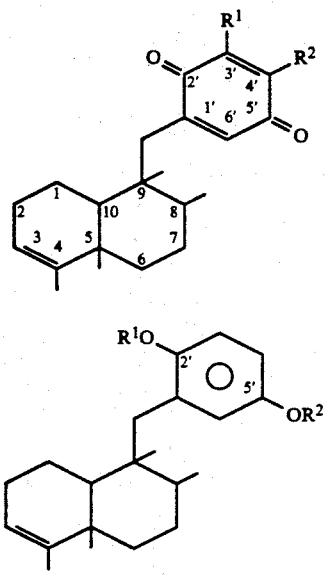

The process for the manufacture of alkylaminoavarones of the general formula Ia is characterized in that avarone is reacted with alkylamine hydrochloride of the general formula $RNH_2 xHCl$, the resulting compounds being converted, if desired, into salts using physiologically-tolerable acids. Compounds of the general formula $RNH_2 xHCl$ can be ethyl, propyl, isopropyl, n-butyl, isobutyl and tert. butylamine hydrochloride (Reaction 1 hereinafter).

Preparation of avarone derivatives of the general formula Ia by placing the substituent —NHR in 3' or 4' position is characterized in that the reaction components are reacted in 50% ethanol in the presence of pyridine (G. Cimino, S. de Rosa, S. de Stefano, L. Cariello and L. Zanetti, Experientia 38, 896 (1982)). The resulting isomer mixtures of 3' and 4' alkylamino avarones can be separated by column chromatography using silica gel. If desired, these reaction products can be converted into their salts by reaction with physiologically tolerable acids. For this purpose suitable acids are hydrochloric acid, hydrobromic acid, sulphuric acid, phosphoric acid, tartaric acid, maleic acid, etc.

The process for the manufacture of avarol derivatives of the general formula Ib, wherein $R^1$ and $R^2$ are acyl, is characterized in that avarol is acylated with an acyl chloride of the general formula RCOCl or with a carboxylic acid anhydride of the general formula RCOO-COR, with the exception of the acetanhydride at the hydroxyl group of the C-2' and/or C-5' position. For this purpose acid chlorides or acid anhydrides of dibasic acids such as, e.g., succinic acid, can be used, whereby one molecule of avarol accounts for only one molecule of the derivative of the dibasic acid (diacyloxy).

Compounds of the general formula RCOCl can be, for example, straight-chain acylchlorides such as acetyl, propionyl, n-butyryl, n-valeroyl and capronoyl chlorides, as well as branched acyl chlorides like isobutyryl, isovaleroyl, or ethylmethylacetyl, and trimethyl acetyl chloride. Compounds of the general formula RCOO-COR can, for example, be straight-chain acid anhydrides such as propionic acid, butyric acid, valeric acid and capronic acid anhydrides as well as branched acid anhydrides like isobutyric acid, valeric acid, or ethylmethyl acetic acid and trimethyl acetic acid anhydrides (Reaction 2 hereinafter).

The preparation of the avarol derivatives of the general formula Ib by introducing substituent —COR is characterized in that the reaction components are reacted in the presence of pyridine (S. de Rosa, L. Minale, R. Riccio and G. Sodano, J. Chem. Soc. Perkin I, 1976, 1408-1414; Organikum, VEB Deutscher Verlag der Wissenschaftern, 13th Edition, Berlin 1974, p. 441-446).

REACTION 1

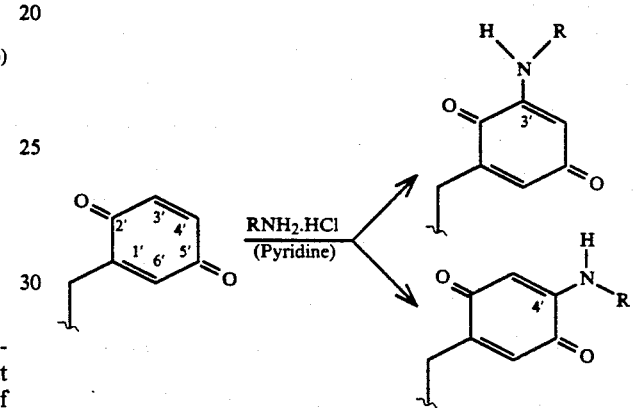

REACTION 2

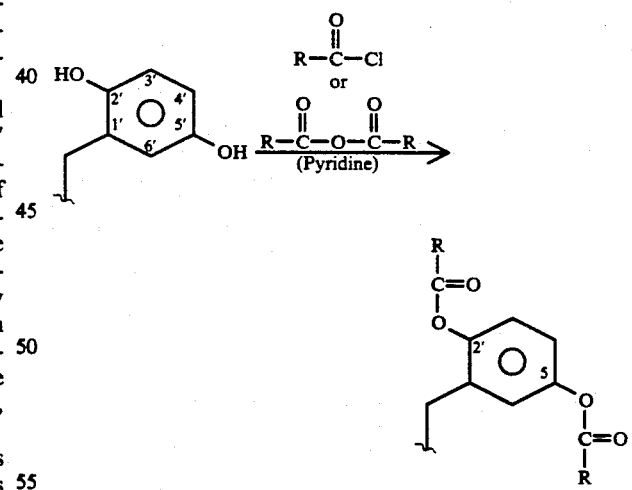

PREPARATION

Preparation of the active principles avarone and avarol of the present invention from known starting materials is effected according to the following specific Examples and pursuant to the following general procedure.

Accordingly, additional subject matter of the invention comprises a process for the manufacture of avarone and avarol characterized in that the fresh marine sponge Dysidea avara is ground, cut into small pieces, or otherwise comminuted, and then extracted with ethyl acetate, solvent being removed from the extract, which extract is preferably reduced to dryness, and the residue being chromatographed over a silica gel column using suitable solvent systems for separating the diketone (hydroquinone) compound from the aromatic diol, such as benzene/ethyl acetate or the like, including, for example, an aromatic solvent such as benzene or an aliphatic solvent such as hexane, together with up to about twenty percent (V/V) of an aliphatic solvent such as diethylether or ethylacetate. By the employment of this method avarone and avarol can be conveniently separated and isolated.

DETAILED DESCRIPTION OF THE INVENTION

The following Examples are given for purposes of illustration only, but are not to be construed as limiting. Examples 2a to 2d of the following examples were obtained according to Reaction 1, whilst examples 3 to 4 were prepared according to Reaction 2. Example 1 relates to the preparation of avarone and avarol from the natural product.

EXAMPLE 1

Avarone and avarol

Extract 3 kg of the sponge with 250 ml of ethyl acetate. Dry the resultant extract over magnesium sulfate and filter. Evaporate the filtrate to dryness. Take up the residue in benzene and subject to chromatography using a silica gel column and benzene as extraction agent. Avarone can be found in the extract whilst avarol is retained on the column. Extract avarol with a mixture of benzene and ethyl acetate (90:10, V:V). Evaporate the extract to dryness Subsequently, pure avarol is obtained by crystallization from dichloromethaneacetone. Purify avarone by recrystallization from benzene.

| Avarone | Avarol |
|---|---|
| Melting point: 62–64° C. | Melting point: 146–148° C. |

Example 2

3'-ethylamino avarone and 4'-ethylamino avarone a) Add 2.5 g of ethylamino hydrochloride and 5 ml of pyridine to a solution of 500 mg avarone in 1000 ml of 50% ethanol, and distill off the ethanol under waterjet vacuum after 20 hours. Extract the aqueous residue with dichloromethane and chromatograph the reduced dichloromethane extract using a silica gel column and dichloromethane as extraction agent. In the course of this process 3'-ethylamino and 4'-ethylamino avarone is obtained.

In the same way the following products have been obtained
b) 3'-propylamino and 4'-propylamino avarone
c) 3'-isopropylamino and 4'-isopropylamino avarone
d) 3'-n-butylamino and 4'-n-butylamino avarone

EXAMPLE 3

Avarol diacetate a) Dissolve 500 mg of avarol in 20 ml of absolute pyridine, and add 1 g of acetyl chloride in portions to the solution under shaking. Treat the mixture as usual, evaporate to dryness and extract the residue with boiling heptane. Cn cooling the ester crystallizes. It is then recrystallized from hexane.

Melting point: 62°–64° C.

In the same way the following products have been obtained:
b) Avarol dipropionate
c) Avarol divalerianate
d) Avarol ditrimethyl acetate

EXAMPLE 4

Avarol dicapronate a) Dissolve 300 mg of avarol in 25 ml of absolute pyridine, and add 0.6 g of caproic acid anhydride in portions to the solution whilst shaking. Treat the mixture as usual, evaporate to dryness, and extract the residue with boiling heptane. Recrystallize from acetone and subsequently from hexane.

In the same way the following products have been obtained:
b) Avarol diisovalerianate
c) Avarol diethyl methyl acetate
d) Avarol succinate

PHARMACEUTICAL COMPOSITIONS

The active ingredients of the invention, together with a conventional adjuvant, carrier, or diluent, may be placed into the form of pharmaceutical compositions and unit dosages thereof, and in such form may be employed as solids, such as tablets or filled capsules, or liquids, such as solutions, suspensions, emulsions, elixirs, or capsules filled with the same, all for oral use; in the form of suppositories for rectal administration; or in the form of sterile injectable solutions for parenteral (including intravenous or subcutaneous) use. Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed. Tablets containing ten (10) milligrams of active ingredient or, more broadly, ten (10) to one hundred (100) milligrams, per tablet, are accordingly suitable representative unit dosage forms.

METHOD OF TREATING

Due to their high degree of activity and their low toxicity, together presenting a most favorable therapeutic index, the active principles of the invention may be administered to a subject, e.g., a living animal body, in need thereof, for the treatment, alleviation, or amelioration, palliation, or elimination of an indication which is susceptible thereto, or representatively of an indication set forth elsewhere in this application, preferably concurrently, simultaneously, or together with a pharmaceutically-acceptable carrier or diluent, especially and preferably in the form of a pharmaceutical composition thereof, whether by oral, rectal, or parenteral (including intravenous and subcutaneous) or in some cases even topical route, in an effective cytostatic and/or antimutagenic amount. Suitable dosage ranges are 1–1000 milligrams daily, preferably 10–500 milligrams daily, and especially 50–500 milligrams daily, depending as usual upon the exact mode of administration, form in which administered, the indication toward which the administration is directed, the subject involved and the body weight of the subject involved, and the preference and experience of the physician or veterinarian in charge.

EXAMPLES OF REPRESENTATIVE PHARMACEUTICAL COMPOSITIONS

With the aid of commonly used solvents, auxiliary agents and carriers, the reaction products can be processed into tablets, coated tablets, capsules, drip solutions, suppositories, injection and infusion preparations, and the like, and can be therapeutically applied by the oral, rectal, parenteral and additional routes. Representative pharmaceutical compositions follows.

a) Tablets suitable for oral administration which contain the active ingredient may be prepared by conventional tabletting techniques.

b) For suppositories, any usual suppository base may be employed for incorporation thereinto by usual procedure of the active ingredient, such as a polyethyleneglycol which is a solid at normal room temperature but which melts at or about body temperature.

c) For parenteral (including intravenous and subcutaneous) sterile solutions, the active ingredient together with conventional ingredients in usual amounts are employed, such as sodium chloride, sodium dihydrogen phosphate, disodium edetate (ethylenediaminetetraacetic acid disodium salt), benzyl alcohol, sodium hydroxide to adjust pH, and double-distilled water q.s., according to conventional procedure, such as filtration, aseptic filling into ampoules or IV-drip bottles, and autoclaving for sterility.

Other suitable pharmaceutical compositions will be immediately apparent to one skilled in the art.

The following examples are again given by way of illustration only and are not to be construed as limiting.

EXAMPLE 1

Tablet formulation

A suitable formulation for a tablet containing 10 milligrams of active ingredient is as follows:

|  | Mg. |
|---|---|
| Active Ingredient | 10 |
| Lactose | 18 |
| Potato starch | 38 |
| Gelatin | 2 |
| Talcum | 2 |
| Magnesium stearate | 0.1 |

EXAMPLE 2

Tablet formulation

Another suitable formulation for a tablet is as follows:

|  | Mg. |
|---|---|
| Active Ingredient | 10 |
| Potato starch | 40 |
| Polyvinylpyrrolidone | 5 |
| Sugar coated and colored. | |

EXAMPLE 3

Capsule formulation

A suitable formulation for a capsule containing 10 milligrams of active ingredient is as follows:

|  | Mg. |
|---|---|
| Active Ingredient | 10 |
| Corn starch | 90 |
| Lactose | 50 |
| Talcum | 2 | filled in a gelatin capsule.

EXAMPLE 4

Solution for injection

A suitable formulation for an injectable solution containing one percent of active ingredient is as follows:

| Active Ingredient | mg 12 |
|---|---|
| Sorbitol | mg 40 |
| Sterile water to make | mg 1 |

EXAMPLE 5

Liquid oral formulation

A suitable formulation for 1 liter of a liquid mixture containing 2 milligrams of active ingredient in one milliliter of the mixture is as follows;

|  | G. |
|---|---|
| Active Ingredient | 2 |
| Saccharose | 250 |
| Glucose | 300 |
| d-Sorbitol | 150 |
| Agar-agar | 0.15 |
| Methylparaben | 0.5 |
| Propylparaben | 0.05 |
| Orange flavor | 10 |
| Tartrazine yellow. | |
| Purified water to make a total of 1000 ml. | |

EXAMPLE 6

Liquid oral formulation

Another suitable formulation for 1 liter of a liquid mixture containing 2 milligrams of active ingredient in one milliliter of the mixture is as follows:

|  | G. |
|---|---|
| Active Ingredient | 2 |
| Tragacanth | 7 |
| Glycerol | 50 |
| Saccharose | 400 |
| Methylparaben | 0.5 |
| Propylparaben | 0.05 |
| Black currant-flavor | 10 |
| Red No. 2 C.I. 184 | 0.02 |
| Purified water to make a total of 1000 ml. | |

EXAMPLE 7

Liquid oral formulation

Another suitable formulation for 1 liter of liquid mixture containing 2 milligrams of active ingredient in one milliliter of the mixture is as follows:

|  | G. |
|---|---|
| Active Ingredient | 2.4 |
| Saccharose | 400 |

-continued

|  | G. |
|---|---|
| Bitter orange peel tincture | 20 |
| Sweet orange peel tincture | 15 |
| Purified water to make a total of 1000 ml. | |

PHARMACOLOGY—SUMMARY

The active principle of the present invention, avarol, and pharmaceutical compositions thereof and method of treating therewith, is characterized by unique advantageous and unpredictable properties, rendering the "subject matter as a whole", as claimed herein, unobvious. The compounds and pharmaceutical compositions thereof have exhibited, in standard accepted reliable test procedures, the following valuable properties and characteristics:
Antitumor
Antimitotic
Cytostatic
Antimutagenic
Antilymphoma
Antileukemic
Anti human malignant brain tumor
and are accordingly of utility elimination, palliation, alleviation, and amelioration of responsive conditions by application or administration to the host or to the situs.

PHARMACOLOGY

Pharmacological Actions (A)—Antitumor

The reaction products according to the general formula I and particularly avarone and avarol, show valuable pharmacological properties. The antitumor activity has been shown in vitro using the L5178y and L121o lymphoma cell system in mice. These cells were suspension cultures, as described previously (W. E. G. Muller and R. Zahn, Cancer Res. 39, 1102 (1979)).

The $ED_{50}$ concentrations of the compounds (inoculation: 4000 cells/ml; incubation time: 72 hours) ranged from 0.7 to 6.7 $\mu$m for both tumor cell strains. In this test avarone, avarol and the avarol esters were the most effective substances. The action mechanism could be demonstrated in incorporation studies. In the presence of the reaction products in $ED_{50}$ concentrations the incorporation of [$^3$H] thymidine into the DNA, of [$^3$] uridine into the RNA, of [$^3$H] phenylalanine into proteins, and of [$^3$H] into glycoproteins is promoted. This effect could be shown by autoradiographic methods (K. Habel and N. P. Salzman, Fundamental Techniques in Virology, Academic Press, New York 1969, p. 242) to be a partial synchronization of the cells during the $G_2$-M phase.

In cytological studies by using Giemsa staining and acridine orange staining of the mitotic chromosomes (R. Rigler, Acta Physiol. Scand. 67 (suppl. 267), 1 (1966), it was found that the reaction products affect the mitotic index of L5178y cells. Therefore, the pharmacological activity of avarone and its derivatives is that of a mitotic toxin. This action mechanism has also been demonstrated in biochemical studies: Avarone and its derivatives inhibit the polymerization of microtubuli in the substoichiometric range as was shown in viscosimetric studies by S. D. Mac.Lean-Fletcher and T. D. Pollard (J. Cell Biol. 85, 414–428 (1980)).

The polymerization of the microtubuli is inhibited on the level of protofilament elongation. By employing higher concentrations of the reaction products the polymerization of microtubuli during other cell phases is inhibited in addition to the inhibition of the polymerization of microtubuli during the mitotic phase. There are no chromosome aberrations after the administration of therapeutic doses of avarone and its derivatives.

Of special importance for the application of the reaction products in the chemotherapy of carcinoses is the fact that there is no cytostatic effect on non-tumor cells in culture when being used in therapeutically-applicable concentrations.

This result was obtained from tests on lymphocyte cultures Spleen lymphocytes were obtained from 6-week old NMRI mice. The erythrocytes were eliminated from the suspension by treatment with ammonium chloride. The spleen lymphocytes were kept in RPMI 164o medium/2o% fetal bovine serum in a density of $1.5 \times 10^7$ cells/ml for 72 hours in the presence of 2 $\mu$g/ml concanavalin A. 18 hours prior to the termination of the test [$^3$H] was added. On incubation with 10 $\mu$m of the reaction products no impairment of the DNA rate of synthesis was determined. In the presence of 15 $\mu$m there was only a 15% inhibition of the incorporation rate of [$^3$H] thymidine into the DNA.

The antitumor action of avarone and its derivatives has also been shown in vivo in experimental animals. The tests were carried out as described previously (W. E. G. Müller, R. K. Zahn, A. Maidhof, H. C. Schröder, M. Bachmann and H. Umezawa, J. Antibiotics 37, 239 (1984)). NMRI mice that had been inoculated with L5178y lymphoma, and—after having developed the tumor—were treated for.5 days with, e.g., 0.3 mg/kg avarone i.p. per day, lived considerably longer than the untreated mice. 5o% of the untreated animals had died after 18 days, whereas 5o% of the treated animals were still alive on the 26th day.

The subacute toxicity values ranging from 35 to 75 mg/kg at 5-day i.p. treatment of mice are so favourable that the application of the reaction products in the chemotherapy of carcinoses is to be expected.

Pharmacological Actions (B)—Antitumor

Avarone and also Avarol are antimitotic agents which cause at $ED_{50}$ concentrations an increase of mitotic indices from 6.5 to 11.9 [10.4], using L5178y mouse lymphoma cell system (Muller et al., Bas. Appl. Histochem. 1985, 29, in press). In in vitro studies, applying the methods of viscosimetry and electron microscopy, it was demonstrated that the compounds inhibit assembly of brain microtubule protein at an at least stoichiometric concentration ratio (Muller et al., Bas. Appl. Histochem. 1985, 29, in press). Moreover, evidence is available that the new antimitotic agents inhibit protofilament elongation rather than lateral association of tubulin during protofilament formation. It is suggested that the compounds interfere with polymerization of tubulin both in interphase and during mitosis. Binding studies in vitro demonstrated Avarol (radiolabelled as [$^3$H]-Dihydroavarol) to interact with tubulin at sites different from those known for Vincristine, Colchicine and Etoposide ® (Table).

TABLE

Binding affinity of [$^3$H]-Avarol
(labelled [$^3$H]-Dihydroavarol)(1 μM)
to tubulin, as measured by binding assay technique

|  | none | plus 30 μM Vincristine | plus 30 μM Colchicine | plus 30 μM Etoposide$^R$ |
|---|---|---|---|---|
| no tubulin | <4 | <4 | <4 | <4 |
| 1 μM tubulin | 61 | 57 | 59 | 63 |
| 10 μM tubulin | 96 | 93 | 97 | 91 |

In cell culture studies it was established that Avarone and its analogue Avarol exhibit potent cytostatic activities both on L5178y mouse lymphoma cells (T-cell lymphoma) and on L1210 mouse leukemia cells (B-cell derivative) (Muller et al., Comp. Biochem. Physiol. 1985, 80C, pp. 47–52 and Cancer Research 1985, 45(10), in press). The following ED50 concentrations (concentration which causes a 50% inhibition of cell growth) were determined for Avarone (Avarol); L5178y cells: 0.62 M (0.93 M) and for L1210: 0.95 M (1.1 M). The corresponding ED$_{50}$ concentrations in experiments with non-lymphoid cells (e.g., melanoma cells, HeLa cells, human fibroblasts, and human gingival cells) were determined to be 15 to 120-fold higher. In L5178y cells, Avarone was the most cytotoxic of the compounds tested; Avarol and Dihydroavarol were moderately cytotoxic, and the methylamino derivatives of Avarone were effective at higher concentrations.

In order to define the activity spectrum of Avarone and Avarol further, their influence on DNA synthesis in T and B lymphocytes was investigated. As mitotic inductors we used concanavalin A (ConA) for T lymphocytes from both mouse spleen and human peripheral blood, lipopolysaccharide (LPS) for murine B lymphocytes, and pokeweed mitogen (PWM) for human T and B lymphocytes (Muller et al., European J. Cancer and Clinical Oncology—in press).

Studying the effect on mouse spleen lymphocytes, we found the following ED$_{50}$ concentrations (inhibition of [$^3$H]-dThd incorporation rate by 50%), for Avarone: non-activated cultures, 2.9 M; ConA-stimulated lymphocytes, 1.9M and LPS-stimulated cells, 4.3 M; and for Avarol: non-activated cultures, 3.8 M; and ConA- or LPS- stimulated lymphocytes, 2.4 M and 5.9 M, resp. Interesting was the finding that at low concentrations both Avarone and Avarol enhanced DNA synthesis in non-activated lymphocytes and especially in LPS-stimulated lymphocytes. The highest stimulatory effect was measured in the drup ranges 1–2M. This means that the two secondary metabolites from Dysidea avara can break—dose dependently—the restrictive control mechanism(s) of DNA synthesis in particular eukaryotic cells.

TOXICITY

The in vivo toxicity (mg compound/kg) of Avarol on male NMRI mice is as follows; acute toxicity: LD$_{50}$ (269.2), LD$_{10}$ (156.4) and subacute toxicity: LD$_{50}$ (218.4), LD$_{10}$ (138.6) (Muller et al., Cancer Research 1985, 45(10), in press).

ANTILEUKEMIC ACTIVITY

The antileukemic activity of Avarone and Avarol was studied in vivo using the L5178y cell system in NMRI mice (Muller et al., ibid.). The median life span of the L5178y lymphoma-bearing control mice was 14.3 days. Both Avarone and Avarol were determined to increase the life span of the tumor-bearing mice considerably. The animals were i.p. injected with the compounds for 5 consecutive days starting at day 1 or day 8. In general, the treatment starting at day 1 after tumor inoculation was superior to that beginning at day 8, as can be deduced fom the values for the % ILS (increase in median life span): Schedule day 1–5 (day 8–12) for 10mg Avarone/kg/injection: 146% (69%) and for Avarol: 87% (34%). The schedule of days 1–5 resulted even in a dose-dependent cure of 20–70% of the tumor-bearing mice both with Avarone and Avarol. Using this regimen, the dosage of 10 mg Avarone/kg/day received the highly active activity rating, which bases on the determined log$_{10}$ kill values. Avarol was somewhat less efficient. The 90% effective doses of both Avarone and Avarol on tumor growth were estimated according to Skipper and Schmidt (Cancer Chemotherapy Rep. 1962, 17, pp. 1–173) and found to be for Avarone 9.4 mg/kg/day and for Avarol 31 mg/kg/day. From these data and the LD$_{10}$ values, the therapeutic ratios were calculated for Avarone to be 11.7 and for Avarol, 4.5. These values are in the range of those determined for cyclophosphamide, daunomycin and methotrexate (Rubidomycin. Berlin, Springer-Verlag 1969).

ANTIMUTAGENIC

Avarone and its analogue were determined in the Ames test to be neither direct nor indirect (S-9 activating system) mutagens (Muller et al., Cancer Res. 1985, 45(10), in press, and Mut. Res. Letters 1985, 144, pp. 63–66). Furthermore Avarone and its analogues were no inducers of benzo(a) pyrene monooxygenase (BaPMO) activity in experimental fish. At doses of 50 or 100 mg/kg of Avarone and its analogues, a BaPMO activity of 30.2 pg of 3-OH-BaP formed per mg protein x min was measured; the enzyme in the control animals showed an activity of 35 pg/mg×min. For the assessment of the potential antimutagenic property, Avarone and Avarol were incubated in combination with benzo(a)pyrene in the Ames-microsomal assay. Benzo(a)-pyrene alone was found to induce in the presence of S-9 fraction 1325 his+ revertants at a concentration of 10 μM. Applied in combination with Avarone or Avarol, the mutagenic effect of benzo-(a)pyrene was drastically reduced. Addition of 5 μM of either of the two compounds reduced the number of the revertants to 22–26%, while at 30 μM and 150 μM a reduction to 14% and 11%, respectively, was determined. Hence, both Avarone and Avarol are powerful antimutagenic agents exhibiting an activity as strong as the known cytochrome P-450 dependent monooxygenase inhibitor benzoflavone. The assumption, drawn from the data of mutagenicity testing, that both Avarone and Avarol are potent inhibitors of BaPMO, was confirmed by enzymic studies. Concentrations of 50 μM reduced the activity to 18% (Avarone) and to 20% (Avarol), respectively.

The hitherto elucidated characteristics provide Avarone and Avarol with promising properties indicative of potential utility for an application thereof in human cancer treatment. They are; (a) the compounds are present in a high yield in the sponge Dysidea avara, which is very abundant; (b) Avarone and Avarol display potent antileukemic activity in vitro; 8c) they cause biphasic and differential effects on DNa metabolism of human and murine T and B lymphocytes; (d) the cytostatic agents are highly active also as antileukemic agents in vivo; (e) they act as antimitotic compounds on the level of microtubule formation; (f) the two agents were determined to be neither direct mutagens nor premutagens; (g) moreover, they display antimutagenic activity and (h) the two compounds display also antibacterial and antifungal activity against a limited range of microorganisms.

PHARMACOLOGICAL ACTIONS—ANTITUMOR (Human Brain)

The antitumor activity of Avarone and Avarol is also pronounced towards malignant human brain tumors.

A glioblastoma line was used for the tissue culture studies. The cells derived from a patient with primary and metastatic malignant glioblastoma tumor. Biopsy material was disaggregated and cultivated in MEM-medium plus 20% fetal calf serum. The cells were seeded at a concentration of 500,000 cells per 3.5 cm petri dish and incubated for 48 hours in the absence or presence of Avarol or Avarone. Then the cell number was determined. The detailed description of the test procedure was given earlier (A. Totsuka, W. E. G. Muller, R. K. Zahn: Bleomycin, action on growth of oncogenic RNA viruses and on cell proliferation. Archives of Virology 48, 169-179; 1975).

Results: At a concentration of 3.5 microgram per ml the inhibition of the cell growth was:
for Avarone: 86% and
for Avarol: 71%.

The future application of Avarone and/or Avarol in human chemotherapy of brain tumors is very promising, because the compounds can penetrate the blood-brain-barrier. The experiments were performed in vivo.

The experiments were performed with dihydro-avarol (tritium labelled; specific radioactivity: 3.2 Ci/mmol). As test animals Balb/c mice (male; 25 g) were chosen.

The radioactive Avarol was injected intraperitoneally (i. p.) at a concentration of 10 mg/kg. 1 hour thereafter the concentration in the organs was determined by the radioactivity.

Results:

| Organ | Concentration of tritium-labelled dihydro-avarol (microgram per g tissue) |
|---|---|
| Liver | 12.3 |
| Lung | 7.4 |
| Skin | 2.8 |
| Brain | 4.2 |

These data indicate that the compound is transported into the brain after i.p. injection. Together with the tissue culture data, a curative effect of Avarol and/or Avarone towards brain tumors in vivo can be expected.

MATERIALS AND METHODS

Materials

Concanavalin TM A [ConA] (no. C 5275), lipopolysaccharide LPS (no. L 4130) and pokeweed mitogen (no. L 9379) were obtained from Sigma, St. Louis, Mo. (U.S.A.); [methyl-$^3$H]thymidine (spec. act. 87 Ci/mmole) from the Radiochemical Centre, Amersham (England); colcimide from Ciba Geigy, Wehr (Germany) and phytohemagglutinin (PHA 15) from Deutsche Wellcome, Burgwedel (Germany).

Avarol was isolated from Dysidea avara which was collected in the Bay of Kotor (Yugoslavia). Avarone was obtained from its corresponding hydroquinone avarol by $Ag_2O$ oxidation.

Cultivation of lymphocytes from mouse spleen

Spleen lymphocytes were prepared from 5-6 weeks old male outbred NMRI mice as previously described. The erythrocyte-free and macrophage-containing lymphocytes ($2.5 \times 10^6$ cells) were placed in a final volume of 200 $\mu$l on microtiter plates and incubated for 72 hr in Dulbeccos TM minimum essential medium (DMEM), supplemented with 2 mM glutamine and 10 % fetal calf serum. 18 hr prior to the end of the incubation 0.1 $\mu$Ci of [$^3$H]-dThd was added to each cup. Where indicated 2 $\mu$g/ml of ConA TM or 20 $\mu$g/ml of LPS were added to the cultures. The cytostatic agents avarone and avarol were dissolved in dimethyl sulfoxide and added at time zero to the cultures. The final concentration of dimethyl sulfoxide was 0.1 %, at this concentration dimethyl sulfoxide was found not to influence the [$^3$H]-dThd incorporation rate. Incorporation of [$^3$H]-dThd was determined as previously described.

Each value came from 6 parallel experiments. The ED$_{50}$ concentrations causing a 50% reduction of [$^3$H]-dThd incorporation were estimated by logit regression.

Preparation of human lymphocytes from circulating blood

From freshly drawn heparinized blood (10 IU of heparin sodium salt/ml blood) the lymphocytes were isolated according to the previously described procedure of Ficoll-Ronpacon. The resulting lymphocytes were suspended at a density of $4 \times 10^6$ cells/ml DMEM, supplemented with 10% fetal calf serum. $1 \times 10^6$ cells in 200 $\mu$l were placed on microtiter plates and processed as described above. The cultures were incubated either in the absence or presence of mitogen (2 $\mu$g/ml of ConA or 3 $\mu$g/ml of PWM).

Determination of mitotic index

Purified human peripheral blood lymphocytes were incubated for 70 hr in DMEM supplemented with 10 % fetal calf serum at a density of $1 \times 10^6$ cells/ml in the presence of colcimide (0.1 $\mu$g/ml) and phytohemagglutinin (2 $\mu$g/ml). During the last 3 hr of incubation, different concentrations of avarol were added to the 5-ml assays. The cells were then processed as follows: 20 min exposure to hypotonicity achieved by adding 3 volumes of distilled water to the cultures; fixation was in 60 % acetic acid 0.1 N hydrochloric acid for 15 min; staining with 2 % acetic orcein. Squash preparations were made on siliconized slides.

For the determination of the mitotic index, 1000 to 1500 cells were analyzed per assay.

Statistical evaluation

T-tests to determine the significance of the growth inhibition effects in the presence or absence of mitogens were performed according to the student's KOLLER S. Statistische Ayuswertmethoden. In: Biochemisches Taschenbuch (ed. by H. M. Rauen), pp. 959-1045. Springer-Verlag, Berlin (1964).

RESULTS

Increase of mitotic index by avarol treatment

After a 3 hr incubation of peripheral blood lymphocytes in the presence of avarol, the mitotic index substantially increased. At drug concentrations of 1.5 $\mu$M, 3.0 μM or 6.0 μM the mitotic index increased to 6.27, 8.91 or 9.45. The mitotic index of the controls (absence of avarol) was 3.51.

Effect of avarone and avarol on mouse spleen lymphocytes

In the absence of mitogen the [$^3$H]-dThd incorporation rate in the lymphocyte cultures was determined to be $1.3 \pm 0.1 \times 10^3$ dpm/$2.5 \times 10^6$ cells per 18 hr. Addition of 2 μg ConA/ml or 20 μg LPS/ml to the cultures augmented the incorporation rate to $21.7 \pm 1.9 \times 10^3$ dpm or $45.8 \pm 3.6 \times 10^3$ dpm/$2.5 \times 10^6$ cells per 18 hr resp.

As summarized in FIG. 1, avarone was the more potent inhibitor of DNA synthesis (measured by the [$^3$H]-dThd incorporation rate) than avarol irrespectively of the activation state of the lymphocytes. The following $ED_{50}$ concentrations were estimated from the dose-response experiments; for avarone: non-activated cultures, $2.9 \pm 0.2$ μM; ConA stimulated lymphocytes, $1.9 \pm 0.2$ μM; and LPS-stimulated cells, $4.3 \pm 0.3$ μM; and for avarol: non-activated cultures; $3.8 \pm 0.3$ μM; and ConA- or LPS-stimulated lymphocytes, $2.4 \pm 0.2$ μM and $5.9 \pm 0.4$ μM, resp. In all three cases the differences in the inhibitory potencies between avarone and avarol were statistically significant (P-value: $<0.001$).

Interesting was the finding that both avarone and avarol at low concentrations enhanced DNA synthesis in non-activated lymphocytes and especially in LPS-stimulated lymphocytes. The highest stimulatory effect was measured in the drug ranges 1-2 μM; maximal stimulation for avarone was determined to be 203; (control: 100%; P value versus control $<0.001$) at a concentration of 1.8 μM, and for avarol, 168: (P: $<0.001$) at the same concentration.

Effect on human peripheral blood lymphocytes

The basis incorporation rates in the human lymphocyte cultures were as follows; without mitogen, $1.4 \pm 0.2 \times 10^3$ dpm/$1 \times 10^6$ cells per 18 hr and in the presence of 2 μg ConA/ml or 3 μg PWM/ml, $17.4 \pm 1.4 \times 10^3$ dpm or $35.9 \pm 2.6 \times 10^3$ dpm/$1 \times 10^6$ cells per 18 hr, resp.

As already determined in the experiments with mouse spleen cells, avarone exhibited a significantly higher inhibitory potency (P: $<0.001$) also on human lymphocytes than avarol. The following $ED_{50}$ values were determined for avarone (avarol): non-activated lymphocytes, $3.2 \pm 0.3$ ($4.9 \pm 0.4$) μM; ConA-stimulated cells, $2.3 \pm 0.2$ ($4.0 \pm 0.3$) μM and PWM-stimulated cells, $4.2 \pm 0.3$ ($5.8 \pm 0.4$) μM (FIG. 2).

Just as in the experiments with murine lymphocytes, the human non-activated and PWM-activated lymphocytes were also determined to have an augmented dThd-incorporation rate at low avarone/avarol concentrations. Again, this enhancing effect on DNA synthesis was measured between 1 and 2 μM. Compared to murine lymphocytes, the degree of stimulation of human lymphocytes with avarone/avarol was less pronounced and amounted for PWM-activated cells at 1.8 μM of avarone (avarol) 136% (126%) control: 100 %; P value versus control $<0.001$].

Figure 1:
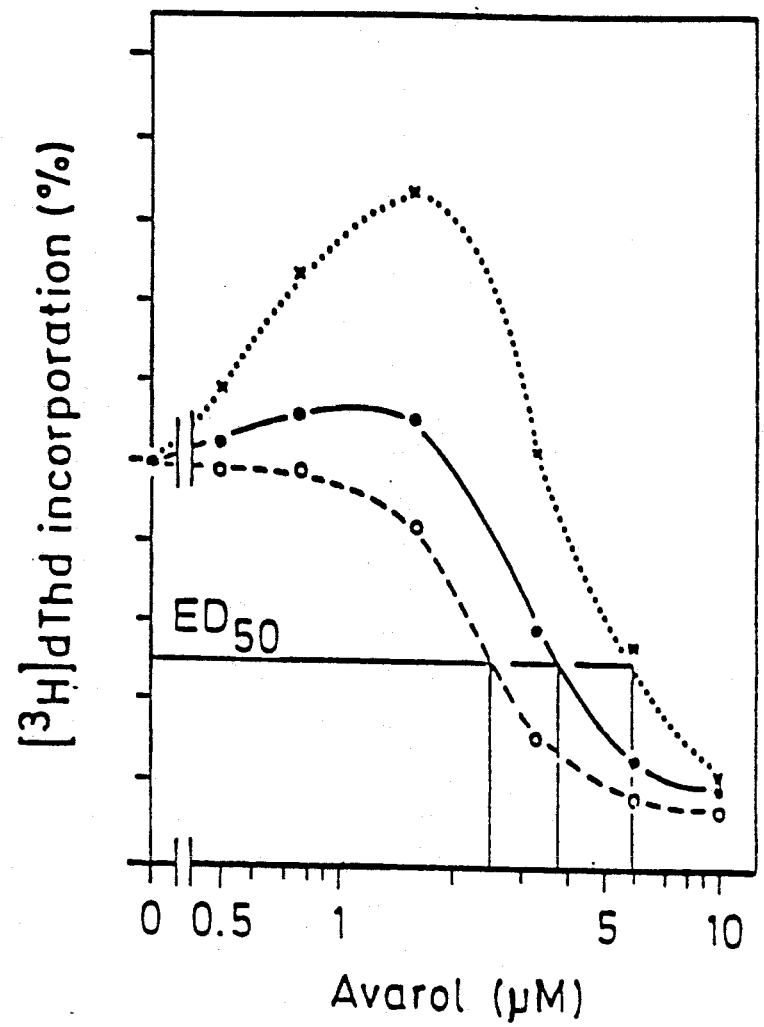
FIG. 1 Effect of avarol on [$^3$H]-dThd incorporation into murine spleen lymphocytes in the absence, (• •), or the presence of 2 μg concanavalin A/ml (○—○) or 20 μg lipopolysaccharide/ml (x . . . x). Addition of [$^3$H]-dThd: 18 hr prior to the end of the incubation. Avarol was added at time zero. Means of quadruplicate experiments are presented; the S.D. varied between 6 and 8%. The values for a 50% inhibition of [$^3$H]-dThd incorporation of the corresponding dose-response experiments are given as vertical lines.
Figure 2:
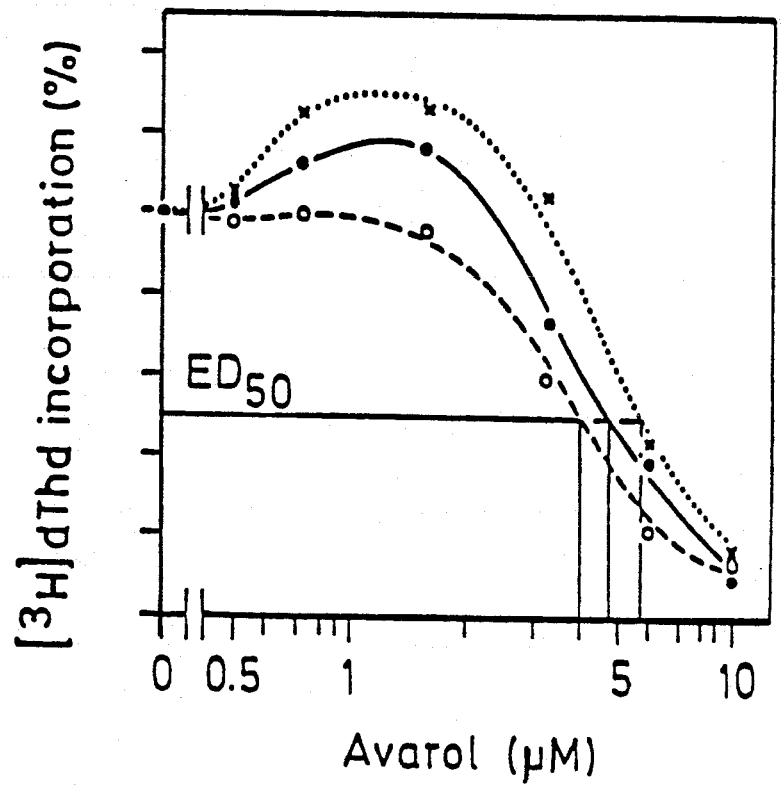
FIG. 2. Effect of avarol on [$^3$H]-dThd incorporation into human peripheral blood lymphocytes in the absence (•—•), or the presence of 2 μg concanavalin A/ml (○—○) or 3 μg pokeweed mitogen/ml (x . . . x). Further details are given in the legend to FIG. 1.

In conclusion, from the foregoing, it is apparent that the present invention provides novel, valuable, and unpredictable applications and uses of the compound avarol, which compound comprises the active principle according to the present invention, as well as novel pharmaceutical compositions thereof and methods of preparation thereof and of treating therewith, all possessed of the foregoing more specifically-enumerated characteristics and advantages.

The high order of activity of the active agent of the present invention and compositions thereof, as evidenced by the tests reported, is indicative of utility based on its valuable activity in human beings as well as in lower animals. Clinical evaluation in human beings has not been completed, however. It will be clearly understood that the distribution and marketing of any compound or composition falling within the scope of the present invention for use in human beings will of course have to be predicated upon prior approval by governmental agencies, such as the U.S. Federal Food and Drug Administration, which are responsible for and authorized to pass judgment on such questions.

It is to be understood that the invention is not to be limited to the exact details of operation, or to the exact compositions, methods, procedures, or embodiments shown and described, as obvious modifications and equivalents will be apparent to one skilled in the art, and the invention is therefore to be limited only by the full scope of the appended claims.

We claim:

1. A pharmaceutical composition in the form of tablets, capsules, emulsions, elixirs, suppositories, or sterile injectable solutions, suitable as an antitumor composition for adversely influencing growth of tumor cells susceptible thereto comprising an amount of avarol effective for such purpose together with a pharmaceutically-acceptable pharmaceutical carrier.

2. A method of combating tumor cells, the growth of which is adversely affected by avarol and therefore susceptible thereto, comprising administering to the host an effective antitumor amount of avarol.

3. A method of claim 2, wherein the compound is administered in the form of a pharmaceutical composition thereof, in which it is present together with a pharmaceutically-acceptable carrier or diluent.

* * * * *

UNITED STATES PATENT AND TRADEMARK OFFICE
CERTIFICATE OF CORRECTION

PATENT NO. : 5,082,865
DATED : Jan. 21, 1992
INVENTOR(S) : Werner E. G. Müller, Rudolf K. Zahn, Eckart Eich It is certified that error appears in the above-identified patent and that said Letters Patent is hereby corrected as shown below:

```
Column 1, line 15; "principles" should read -- principle --.
Column 1, line 18; "principles" should read -- principle --.
Column 1, line 18; delete "as" at the end of the line.
Column 4, line 62; "2-6C" should read -- 2-6 C --.
Column 6, approximately line 15; "Wissenschaftern," should read
    -- Wissenschaften, --.
Column 7, line 67; "Cn cooling" should read -- On cooling --.
Column 9, approximately line 10; "follows," should read --follow.--.
Column 11, approximately line 26; "utility elimination, should read
    -- utility in the treatment, elimination, --.
Column 11, line 49; "[³H] into" should read --[³H] mannose into--.
Column 12, approximately line 14; "cultures  Spleen" should read
    -- cultures: Spleen --.
Column 14, line 5; "fom" should read -- from--.
Column 15, line 65; "and  :phytohemagglutinin" should read
    -- and phytohemagglutinin --.
Column 15, line 67; "avara which" should read -- avara, which --.
Column 16, approximately line 59; "student's" should read --Student's --.
Column 17, line 62; "(126%) control:" should read -- (126%) [control: --.
Column 18, line 4; "(o  o)," should read -- (o—o), -- .
Column 18, line 52; "thereto" should read -- thereto, -- .
```

Signed and Sealed this

Twenty-first Day of September, 1993

Attest:

BRUCE LEHMAN

Attesting Officer

Commissioner of Patents and Trademarks